United States Patent
Horan et al.

(10) Patent No.: US 11,963,847 B2
(45) Date of Patent: Apr. 23, 2024

(54) TPLO PLATE COMPRESSION SYSTEM AND METHOD

(71) Applicant: DEPUY SYNTHES PRODUCTS, INC., Raynham, MA (US)

(72) Inventors: Timothy J. Horan, Royersford, PA (US); Michael Kowaleski, Harwich, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 248 days.

(21) Appl. No.: 17/453,453

(22) Filed: Nov. 3, 2021

(65) Prior Publication Data
US 2023/0140439 A1    May 4, 2023

(51) Int. Cl.
*A61D 1/00*   (2006.01)
*A61B 17/00*  (2006.01)
(Continued)

(52) U.S. Cl.
CPC ............ *A61D 1/00* (2013.01); *A61B 17/8014* (2013.01); *A61B 17/8061* (2013.01);
(Continued)

(58) Field of Classification Search
CPC ............ A61B 17/8014; A61B 17/8095; A61B 17/8061; A61B 17/8052; A61B 17/7059;
(Continued)

(56) References Cited

U.S. PATENT DOCUMENTS

| RE31,628 E | 7/1984 | Allgower et al. |
| 4,565,191 A | 1/1986 | Slocum |

(Continued)

FOREIGN PATENT DOCUMENTS

| DE | 10015734 A1 | 9/2001 |
| DE | 20 2005 019277 | 2/2006 |

(Continued)

OTHER PUBLICATIONS

AO Development, "New Products from AO Development", News—No. 1, AO Publishing, Jun. 2004, 28 sheets.
(Continued)

*Primary Examiner* — Marcela I. Shirsat
(74) *Attorney, Agent, or Firm* — Fay Kaplun & Marcin, LLP

(57) ABSTRACT

TPLO plate includes a body having a proximal portion positioned over a cut and repositioned proximal segment of a tibia during a procedure and a distal portion positioned over a distal segment of the tibia during the procedure and a first distal hole extending through a proximal end of the distal portion from the first surface to the second surface. The first hole is configured so that the body is rotatable about a fixation element seated therein in combination with a second distal hole extending through the distal portion distally of the first hole. The second hole includes a compression surface along a caudal side thereof, so that a head portion of a fixation element is slid therealong during insertion into the second hole and the distal end is moved caudally relative to the fixation element and the body is rotated about the fixation element in the first hole relative to the recess of the first hole, cranially compressing the proximal segment against the distal segment.

23 Claims, 4 Drawing Sheets

(51) Int. Cl.
 *A61B 17/70* (2006.01)
 *A61B 17/80* (2006.01)
 *A61D 99/00* (2006.01)

(52) U.S. Cl.
 CPC .... *A61D 99/00* (2013.01); *A61B 2017/00738* (2013.01); *A61B 17/7059* (2013.01); *A61B 17/8052* (2013.01); *A61B 17/8057* (2013.01); *A61B 17/8095* (2013.01)

(58) Field of Classification Search
 CPC ..... A61B 17/157; A61B 17/808; A61B 17/80; A61B 17/8057; A61B 2017/00738; A61D 1/00; A61D 99/00
 USPC .... 606/280, 286, 88, 87, 70, 902, 86 B, 289
 See application file for complete search history.

(56) References Cited

U.S. PATENT DOCUMENTS

| | | |
|---|---|---|
| 4,677,973 A | 7/1987 | Slocum |
| 4,762,122 A | 8/1988 | Slocum |
| 4,800,874 A | 1/1989 | David et al. |
| 4,867,144 A | 9/1989 | Karas et al. |
| 4,955,888 A | 9/1990 | Slocum |
| 4,988,350 A | 1/1991 | Herzberg |
| 5,002,544 A | 3/1991 | Klaue et al. |
| 5,190,544 A | 3/1993 | Chapman et al. |
| 5,304,180 A | 4/1994 | Slocum |
| 5,364,398 A | 11/1994 | Chapman et al. |
| 5,578,038 A | 11/1996 | Slocum |
| 5,601,553 A | 2/1997 | Trebing et al. |
| 5,709,686 A | 1/1998 | Talos et al. |
| 5,733,287 A | 3/1998 | Tepic et al. |
| 5,749,872 A | 5/1998 | Kyle et al. |
| 5,752,953 A | 5/1998 | Slocum |
| 5,827,286 A | 10/1998 | Incavo et al. |
| 5,868,749 A | 2/1999 | Reed |
| 5,904,684 A | 5/1999 | Rooks |
| 5,938,664 A | 8/1999 | Winquist et al. |
| 5,951,557 A | 9/1999 | Luter |
| 5,968,047 A | 10/1999 | Reed |
| 6,001,099 A | 12/1999 | Huebner |
| 6,077,266 A | 6/2000 | Medoff |
| 6,093,201 A | 7/2000 | Cooper et al. |
| 6,096,040 A | 8/2000 | Esser |
| 6,183,475 B1 | 2/2001 | Lester et al. |
| 6,221,073 B1 | 4/2001 | Weiss et al. |
| 6,283,969 B1 | 9/2001 | Grusin et al. |
| 6,623,486 B1 | 9/2003 | Weaver et al. |
| 6,669,701 B2 | 12/2003 | Steiner et al. |
| 6,719,759 B2 | 4/2004 | Wagner et al. |
| 6,974,461 B1 | 12/2005 | Wolter |
| 7,090,676 B2 | 8/2006 | Huebner et al. |
| 7,108,697 B2 | 9/2006 | Mingozzi et al. |
| 7,128,744 B2 | 10/2006 | Weaver et al. |
| 7,189,237 B2 | 3/2007 | Huebner |
| 7,195,633 B2 | 3/2007 | Medoff et al. |
| 7,267,678 B2 | 9/2007 | Medoff |
| 7,335,204 B2 | 2/2008 | Tornier |
| 7,341,589 B2 | 3/2008 | Weaver et al. |
| 7,537,596 B2 | 5/2009 | Jensen |
| 7,655,029 B2 | 2/2010 | Niederberger et al. |
| 7,695,502 B2 | 4/2010 | Orbay et al. |
| 7,722,653 B2 | 5/2010 | Young et al. |
| 7,740,648 B2 | 6/2010 | Young et al. |
| 7,951,179 B2 | 5/2011 | Matityahu |
| 8,177,818 B2 | 5/2012 | Wotton, III |
| 10,226,288 B2 | 3/2019 | Sidebotham et al. |
| 10,258,396 B2 | 4/2019 | Kazanovicz et al. |
| 10,299,841 B2 | 5/2019 | Dunlop et al. |
| 10,751,098 B2 | 8/2020 | Gahman et al. |
| 11,096,729 B2 | 8/2021 | Dunlop et al. |
| 11,298,167 B2 | 4/2022 | Dunlop et al. |
| 2002/0013587 A1 | 1/2002 | Winquist et al. |
| 2002/0045901 A1 | 4/2002 | Wagner et al. |
| 2002/0156474 A1 | 10/2002 | Wack et al. |
| 2004/0059335 A1 | 3/2004 | Weaver et al. |
| 2004/0116930 A1 | 6/2004 | O'Driscoll et al. |
| 2004/0167522 A1 | 8/2004 | Niederberger et al. |
| 2004/0193165 A1 | 9/2004 | Orbay |
| 2004/0225291 A1 | 11/2004 | Schwammberger et al. |
| 2004/0260291 A1 | 12/2004 | Jensen |
| 2005/0010226 A1 | 1/2005 | Grady, Jr. et al. |
| 2005/0015089 A1 | 1/2005 | Young et al. |
| 2005/0049594 A1 | 3/2005 | Wack et al. |
| 2005/0107796 A1 | 5/2005 | Gerlach et al. |
| 2005/0234458 A1 | 10/2005 | Huebner |
| 2005/0240187 A1 | 10/2005 | Huebner et al. |
| 2006/0009771 A1 | 1/2006 | Orbay et al. |
| 2006/0129151 A1 | 6/2006 | Allen et al. |
| 2006/0149275 A1 | 7/2006 | Cadmus |
| 2006/0173458 A1 | 8/2006 | Forstein et al. |
| 2006/0241608 A1 | 10/2006 | Myerson et al. |
| 2006/0264949 A1 | 11/2006 | Kohut et al. |
| 2007/0083204 A1 | 4/2007 | Sidebotham |
| 2007/0123886 A1 | 5/2007 | Meyer et al. |
| 2007/0162016 A1 | 7/2007 | Matityahu |
| 2007/0233106 A1* | 10/2007 | Horan ............... A61B 17/8061 606/282 |
| 2008/0249573 A1 | 10/2008 | Buhren et al. |
| 2008/0300637 A1 | 12/2008 | Austin et al. |
| 2016/0128745 A1* | 5/2016 | Sidebotham ....... A61B 17/8014 606/281 |
| 2019/0374266 A1 | 12/2019 | Paton |
| 2020/0281634 A1 | 9/2020 | Langdale et al. |
| 2021/0228248 A1 | 7/2021 | Horan et al. |

FOREIGN PATENT DOCUMENTS

| | | |
|---|---|---|
| EP | 1 986 557 | 7/2010 |
| FR | 2405062 | 5/1979 |
| FR | 2405705 | 5/1979 |
| FR | 2406429 | 5/1979 |
| FR | 2758712 | 7/1998 |
| WO | 96/24295 | 8/1996 |
| WO | 01/19267 | 3/2001 |
| WO | 03/013623 | 2/2003 |
| WO | 2004/024009 | 3/2004 |
| WO | 2005/048888 | 6/2005 |
| WO | 2007/137437 | 12/2007 |
| WO | 2015/069728 | 5/2015 |
| WO | 2021/221920 | 11/2021 |

OTHER PUBLICATIONS

Auer et al., "History of AOVET: The First 40 Years", AO Foundation, 2013, 96 sheets.
Ballagas et al., "Pre- and Postoperative Force Plate Analysis of Dogs with Experimentally Transected Cranial Cruciate Ligaments Treated Using Tibial Plateau Leveling Osteotomy", Veterinary Surgery, vol. 33, 2004, pp. 187-190.
Declaration of Troy D. Drewry regarding Claims 1-11, 19, 20 of U.S. Pat. No. 8,523,921, Jul. 12, 2019, 132 sheets.
Declaration of Jeffrey N. Peck, DVM, DACVS regarding Claims 1-11, 19, 20 of U.S. Pat. No. 8,523,921, Jul. 11, 2019, 123 sheets.
*DePuy Synthes Products, Inc. v. Veterinary Orthopedic Implants, Inc.*, No. 3-18-cv-01342-HES-PDB (M.D. Fla.), Redacted Excerpts from Plaintiff's Infringement Contentions, 5 sheets.
Ganesh et al., "Biomechanics of bone-fracture fixation by stiffness-graded plates in comparison with stainless-steel plates", BioMedical Engineering OnLine, Jul. 2005, 4:46, 15 sheets.
Harasen, "Tibial Plateau Leveling Osteotomy—Part 1", Canadian Veterinary Journal, vol. 45, Jun. 2004, 2 sheets.
Harasen, "Tibial Plateau Leveling Osteotomy—Part 2", Canadian Veterinary Journal, vol. 45, Aug. 2004, 2 sheets.
Image Processing of Canine Tibia Medial Radius, Jun. 28, 2019, 21 sheets.
Ismail et al., "Outcome of Cloverleaf Locking Plate Fixation for Femoral Neck Fractures in Young Adults", Malaysian Orthopaedic Journal 2012, vol. 6, No. 1, pp. 30-34.

(56) References Cited

OTHER PUBLICATIONS

Jorgensen Laboratories Inc., "JorVet TPLO plate advertisement", ACVS Veterinary Surgery Medical Journal, vol. 34, No. 5, Sep.-Oct. 2005, 2 sheets.
Kergosien et al., "Radiographic and Clinical Changes of the Tibial Tuberosity after Tibial Plateau Leveling Osteotomy", Veterinary Surgery, vol. 33, 2004, pp. 468-474.
Krishnakanth, "Mechanical Considerations in Fracture Fixation", Queensland University of Technology, Brisbane, Australia, 2012, 192 sheets.
Le, "Biomechanics of Fractures and Fixation", Orthopaedic Trauma Association, 2004, 72 sheets.
New Generation Devices, "UCP-Unity Cruciate Plate", New Generation Devices, 2004, 2 sheets.
Newton et al., "Textbook of Small Animal Orthopaedics", J. B. Lippincott Company, 1985, 46 sheets.
Pacchiana et al., "Surgical and postoperative complications associated with tibial plateau leveling osteotomy in dogs with cranial cruciate ligament rupture: 397 cases (1998-2001)", JAVMA, vol. 222, No. 2, Jan. 15, 2003, pp. 184-193.
Palmer, "Understanding tibial plateau leveling osteotomies in dogs", Veterinary Medicine, Jun. 2005, v. 100, No. 6, pp. 426-453.
Priddy et al., "Complications with and owner assessment of the outcome of tibial plateau leveling osteotomy for treatment of cranial cruciate ligament rupture in dogs: 193 cases (1997-2001)", JAVMA, vol. 222, No. 12, Jun. 15, 2003, pp. 1726-1732.
Petition for Inter Partes Review of Claims 1-11 of U.S. Pat. No. 8,523,921,. Veterinary Orthopedic Implants, Inc., Jul. 12, 2019, 78 sheets.
Petition for Inter Partes Review of Claims 12-18 of U.S. Pat. No. 8,523,921, Veterinary Orthopedic Implants, Inc., Jul. 12, 2019, 72 sheets.
Petition for Inter Partes Review of Claims 19 and 20 of U.S. Pat. No. 8,523,921, Veterinary Orthopedic Implants, Inc., Jul. 12, 2019, 75 sheets.
Decision denying VOI's Petition for Inter Partes Review of claims 1-11 of U.S. Pat. No. 8,523,921, USPTO, PTAB, Jan. 21, 2020, 35 sheets.
Decision denying VOI's Petition for Inter Partes Review of claims 12-18 of U.S. Pat. No. 8,523,921, USPTO, PTAB, Jan. 22, 2020, 52 sheets.
Decision denying VOI's Petition for Inter Partes Review of claims 19-20 of U.S. Pat. No. 8,523,921, USPTO, PTAB, Jan. 22, 2020, 36 sheets.
VOI's Supplemental Invalidity Contentions re U.S. Pat. No. 8,523,921, USDC for the Middle District of Florida, Case No. 3:18-CV-01342, Sep. 18, 2019, 54 sheets.
Reif et al., "Comparison of Tibial Plateau Angles in Normal and Cranial Cruciate Deficient Stifles of Labrador Retrievers", Veterinary Surgery, vol. 32, 2003, pp. 385-389.
Reif et al., "Influence of Limb Positioning and Measurement Method on the Magnitude of the Tibial Plateau Angle", Veterinary Surgery, vol. 33, 2004, pp. 368-375.
Slatter, "Textbook of Small Animal Surgery"—3rd ed., Elsevier Science, 2003, 13 sheets.
Smith & Nephew, Inc., "TC-100 Screw & Plating System Catalog", USA, May 1999, 86 sheets.
Staubli et al., "TomoFix: a New LCP-Concept for Open Wedge Osteotomy of the Medial Proximal Tibia—Early Results in 92 Cases", Injury, International Journal of the Care of the Injured 34, 2003, 8 sheets.
Securos, Securos Orthopedic Implant Advertisements, ACVS Veterinary Surgery Medical Journal, 2003, 9 sheets.
Stoffel et al., "Open Wedge High Tibial Osteotomy: Biomechanical Investigation of the Modified Arthrex Osteotomy Plate (Puddu Plate) and the TomoFix Plate", Clinical Biomechanics 19, 2004, pp. 944-950.
Synthes, "Philos + Philos Long. The Anatomic fixation system for the proximal. Humerus with angular stability. Surgical Technique", Stratec Medical, 2005, 18 sheets.
Synthes Catalog—Part 1, 2002, pp. 1-300.
Synthes Catalog—Part 2, 2002, pp. 301-595.
Synthes Catalog, 2004, 700 sheets.
Synthes Veterinary Brochure, Feb. 2004, 12 sheets.
Taljanovic et al., "Fracture Fixation", RadioGrafics, vol. 23, No. 6, 2003, pp. 1569-1590.
Tornkvist et al., "The strength of plate fixation in relation to the number and spacing of bone screws", Journal of Orthopaedic Trauma, vol. 10, Issue 3, Apr. 1996, 14 sheets.
Veterinary Orthopedic Implants, Inc., "Veterinary Orthopedic Implants Bone Plating Set advertisement", ACVS Veterinary Surgery Medical Journal, vol. 33, No. 1, Jan.-Feb. 2004, 2 sheets.
Veterinary Orthopedic Implants, Inc., "Veterinary Orthopedic Implants TPLO Plates advertisement", ACVS Veterinary Surgery Medical Journal, vol. 34, No. 4, Jul.-Aug. 2005, 2 sheets.
Veterinary Orthopedic Implants, Inc., "Veterinary Orthopedic Implants Y Plates advertisement", ACVS Veterinary Surgery Medical Journal, vol. 34, No. 6, Nov.-Dec. 2005, 2 sheets.
Veterinary Orthopedic Implants, Inc., "Veterinary Orthopedic Implants 2006 Catalog", Veterinary Orthopedic Implants, Inc., 2006, 226 sheets.
Wheeler et al., "In Vitro Effects of Osteotomy Angle and Osteotomy Reduction on Tibial Angulation and Rotation During the Tibial Plateau-Leveling Osteotomy Procedure", Veterinary Surgery, vol. 32, 2003, pp. 371-377.
Zimmer, Inc., Warsaw, Ind., Brochures "Zimmer Periarticular Distal Radial Locking Plates Surgical Technique", "Zimmer Periarticular Proximal Humeral Locking Plate Surgical Technique", "Zimmer Periarticular Distal Femoral Locking Plate Surgical Technique", "Zimmer Periarticular Proximal Tibial Locking Plate", "Zimmer Periarticular Distal Tibial Locking Plate", "Zimmer Periarticular Radial Styloid Locking Plate", Copyright 2005, 135 sheets.
Begue et al., "Small Fragment Set", Stryker Plating System, No. 982181, Switzerland, 2004, 20 sheets.
Bruecker et al., "AOVET North America Course—Advanced Techniques in Small Animal Fracture Management", Lecture Abstract Manual, Hilton Columbus at Easton Hotel, Columbus, Ohio, Apr. 7-10, 2016, 322 sheets.
Conkling et al., "Comparison of Tibial Plateau Angle Changes after Tibial Plateau Leveling Osteotomy Fixation with Conventional or Locking Screw Technology", Veterinary Surgery, vol. 39, 2010, pp. 475-481.
Degner, "Tibial Plateau Leveling Osteotomy—TPLO", VetSurgery Central, 2006, 8 sheets.
Dejardin, "Tibial Plateau Leveling Osteotomy", Textbook of Small Animal Surgery/ [edited by] Douglas Slatter—3rd ed., Saunders, USA, 2003, pp. 2133-2143.
Gretchen, "Meniscal Injures", Veterinary Clinics of North America: Small Animal Practice, vol. 23, No. 4, Jul. 1993, pp. 831-843.
Gruen et al., "Small Fragment Set: Operative Technique", Stryker Plating System, No. LTSFST Rev. 1, USA, 2004, 20 sheets.
Kyon, "Tibial Plateau Leveling Osteotomy", Kyon Veterinary Surgical Products, USA, Sep. 2015, 4 sheets.
Pozzi et al., "Effect of Medical Meniscal Release on Tibial Translation After Tibial Plateau Leveling Osteotomy", Veterinary Surgery, vol. 35, 2006, pp. 486-494.
Slone et al., "Orthopedic Fixation Devices", RadioGraphics, vol. 11, No. 5, Sep. 1991, 25 pp. 823-847.
Slocum et al., "Tibial Plateau Leveling Osteotomy for Repair of Cranial Cruciate Ligament Rupture in the Canine", Veterinary Clinics of North America: Small Animal Practice, vol. 23, No. 4, Jul. 1993, pp. 777-795.
Warzee et al., "Effect of Tibial Plateau Leveling on Cranial and Caudal Tibial Thrusts in Canine Cranial Cruciate-Deficient Stifles: An In Vitro Experimental Study", Veterinary Surgery, vol. 30, 2001, pp. 278-286.
DePuy Syntes Vet, "Mini Tibial Plateau Leveling Osteotomy (TPLO) System. Surgical Technique", 2013, 32 sheets.

* cited by examiner

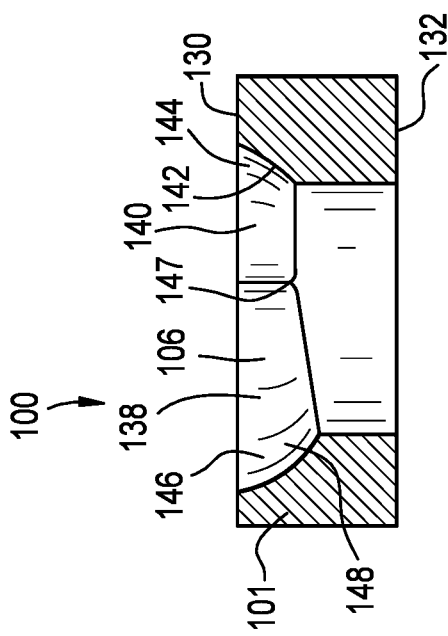
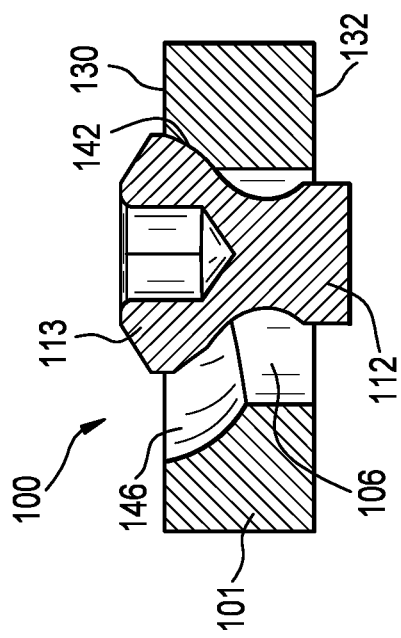
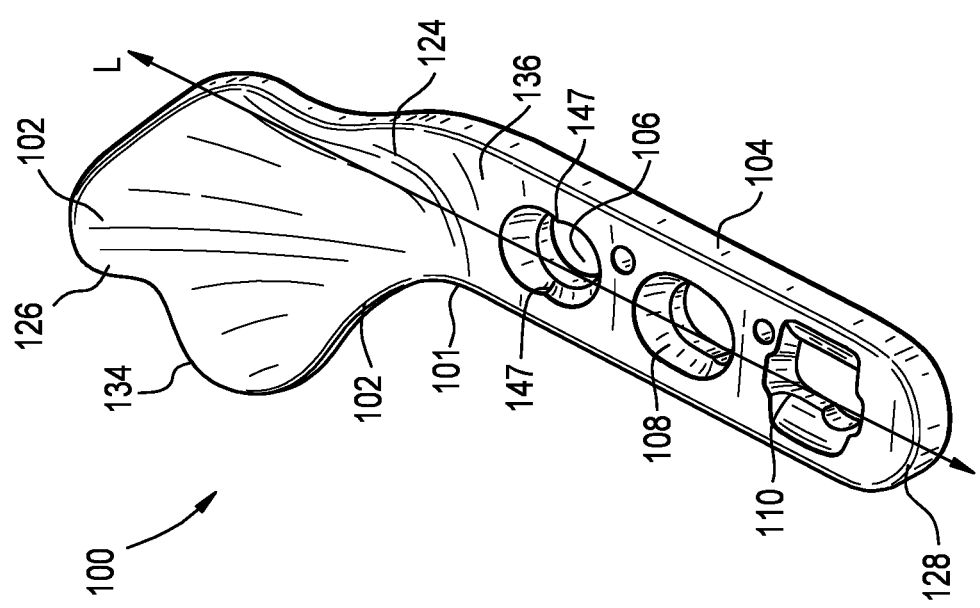

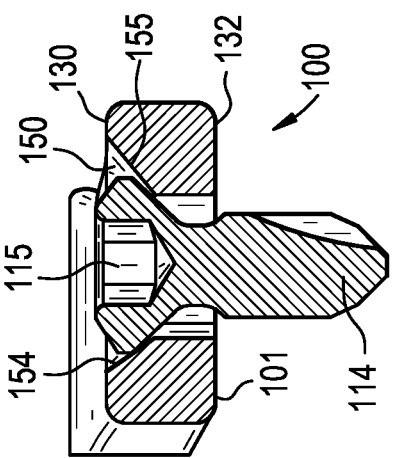
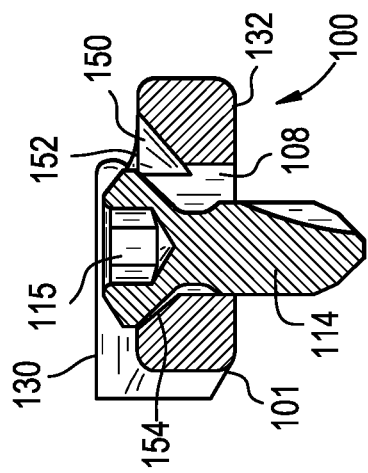
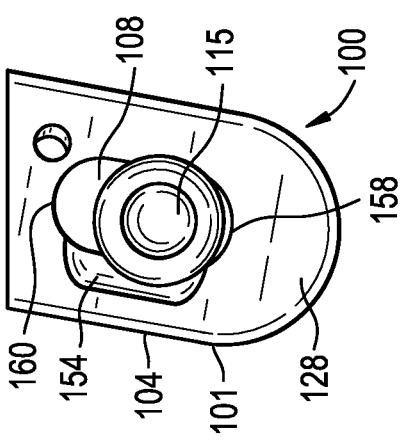
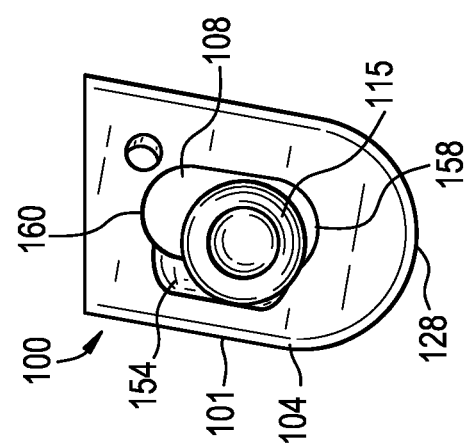
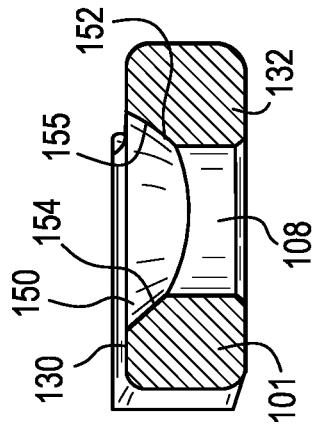
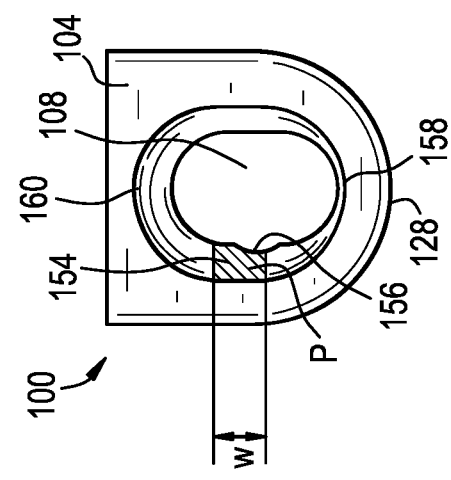

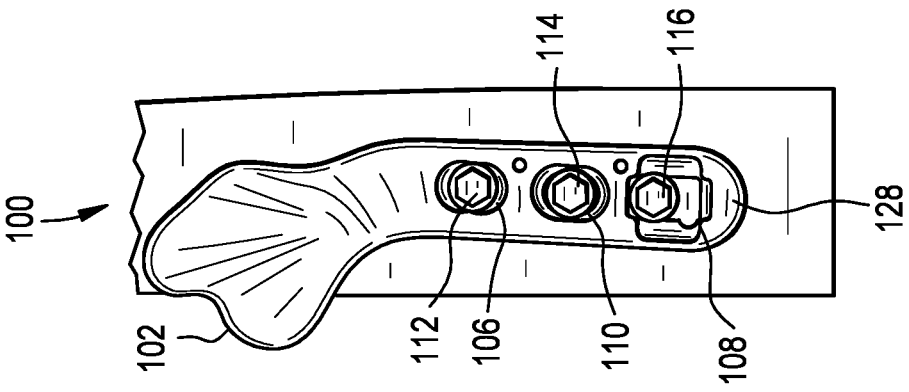
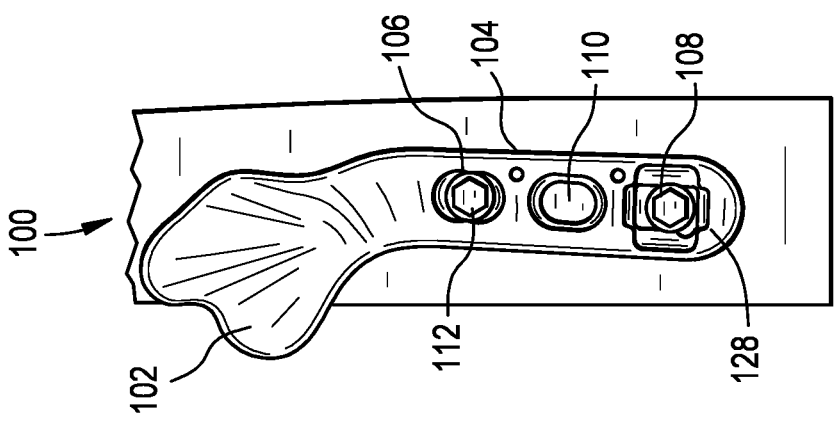
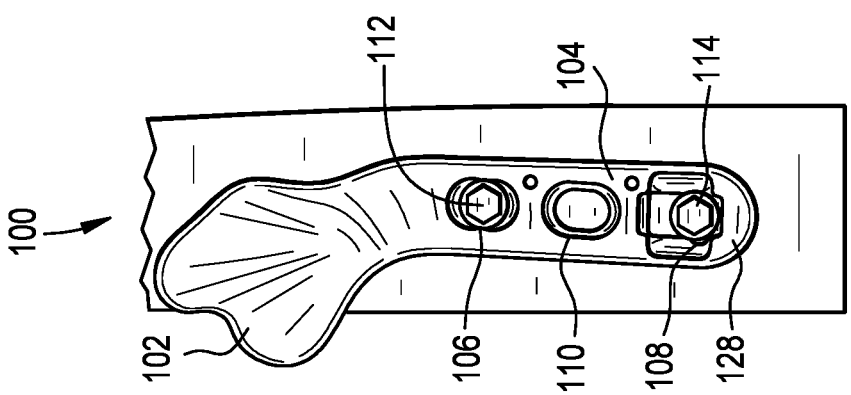
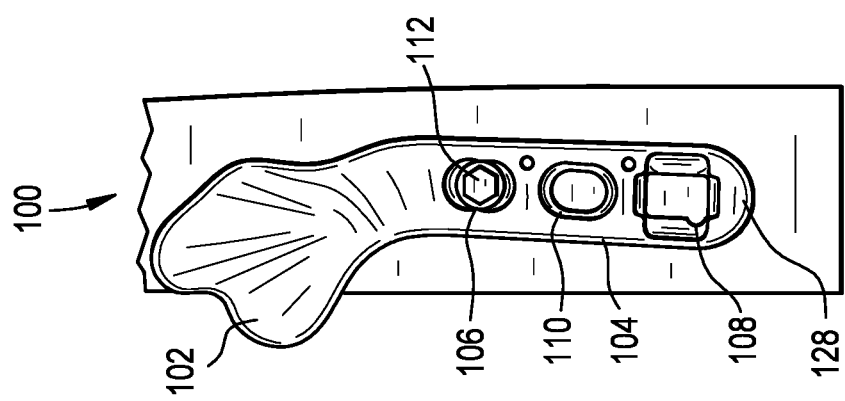

TPLO PLATE COMPRESSION SYSTEM AND METHOD

BACKGROUND

A Tibial Plateau Leveling Osteotomy (TPLO) is a surgical procedure for stabilizing a canine stifle joint, which is comparable to a human knee joint, after a ruptured cranial cruciate ligament (CCL). When the CCL is ruptured or torn, the animal's tibia slides forward with respect to its femur, making it difficult to walk and causing pain. In order to stabilize the joint, a curvilinear cut is made to the upper portion of the tibia. This cut portion of the tibia is then rotated to create a more level plane or surface on the top of the tibia, on which the femur can rest. The cut and repositioned portion of the tibia is then secured to the lower portion of the tibia using a TPLO plate.

TPLO plates are generally sized and shaped to extend along the two portions of the tibia to facilitate healing of the tibia in its new configuration. In some cases, however, where the cut portion is not properly seated in the lower portion of the tibia or where the osteotomy cut is not sufficiently compressed, the bone may fail to heal properly.

SUMMARY OF THE INVENTION

The present disclosure relates to a Tibial Plateau Leveling Osteotomy (TPLO) plate which includes a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion configured to be positioned over a distal segment of the tibia during the TPLO procedure. The TPLO also includes a first distal hole extending through a proximal end of the distal portion of the body from the first surface to the second surface, the first distal hole configured to receive a first distal bone fixation element therein so that the body is rotatable about the first distal bone fixation element relative to a recess of the first distal hole within which a head portion of the first distal bone fixation element is configured to be seated. In addition, the TPLO plate includes a second distal hole extending through the distal portion of the body distally of the first distal hole from the first surface to the second surface, the second distal hole including a sloped compression surface, the second distal hole being configured to receive a second distal bone fixation element therein so that when a head portion of the second distal bone fixation element is slid along the sloped compression surface during insertion of the second distal bone fixation element into the second distal hole, the distal end of the body is moved so that an intersection of the sloped compression surface and the first surface of the body move away from an axis of the second distal bone fixation element rotating the body about the first distal bone fixation element to provide a desired movement of the proximal portion of the body to achieve a desired compression between the cut and repositioned proximal segment of a tibia and the distal segment of the tibia.

In an embodiment, the first distal hole is elongated along a longitudinal axis of the distal portion of the body, the first distal hole including a distal portion including a first rounded relief configured to seat the head portion of the first distal bone fixation element so that, when the first distal bone fixation element is received within the distal portion of the first distal hole, the body is rotatable thereabout.

In an embodiment, each of the first and second distal holes is elongated in a direction parallel to a longitudinal axis of the distal portion of the body.

In an embodiment, the first distal hole includes a proximal portion including a second rounded relief configurated to seat the head portion of the first distal bone fixation element after a desired axial compression has been applied.

In an embodiment, the first and second rounded reliefs of the first distal hole are separated from one another by a transition point that provides resistance to passage of the head of a bone fixation therethrough.

In an embodiment, the transition point is a point at which a width of the first distal hole in a direction transverse to a longitudinal axis of the distal portion of the body is a minimum.

In an embodiment, the second distal hole further includes a groove extending into the sloped compression surface proximal of a distal end of the second distal hole, the groove configured to permit insertion of the second distal bone fixation element through the second distal hole along a caudal side of the longitudinal axis of the distal portion of the body.

In an embodiment, the plate further includes a third distal hole extending through the distal portion of the body, between the first and second distal holes, the third distal hole being configured to receive a third distal bone fixation element therein.

In an embodiment, the third distal hole is elongated in a direction parallel to a longitudinal axis of the distal portion of the body.

In an embodiment, the third distal hole is configured as a dynamic compression hole including a sloped compression surface along a distal portion thereof so that, when the third distal bone fixation element is inserted through a distal portion of the third distal hole, a head portion of the third distal bone fixation element interfaces with the sloped compression surface of the third distal hole to move the body distally relative to the third distal bone fixation element to provide distal compression of the proximal segment of the tibia against the distal segment of the tibia.

In an embodiment, the proximal portion of the body includes three proximal holes, each of which extends through the proximal portion, from the first surface to the second surface, along a proximal edge thereof, each of the proximal holes being configured to receive a proximal bone fixation element therein.

In an embodiment, a first one of the three proximal holes extends through the proximal portion in a position configured to facilitate insertion of a first one of the proximal bone fixation elements therethrough into a caudal portion of the proximal segment of the tibia, wherein a second one of the proximal holes extends through the proximal portion in a position configured to facilitate insertion of a second one of the proximal bone fixation elements therethrough into a proximal portion of the proximal segment of the tibia, and wherein a third one of the proximal holes extends through the proximal portion in a position configured to facilitate insertion of a third one of the proximal bone fixation elements therethrough into a cranial portion of the proximal segment of the tibia.

In an embodiment, a distance between the second distal hole and the first distal hole is equal to a distance between the first distal hole and the third proximal hole.

In an embodiment, the proximal portion of the body is connected to the distal portion of the body via a neck portion curved such that the proximal portion of the body is offset relative to the distal portion of the body toward a caudal side of a longitudinal axis of the distal portion of the body.

In an embodiment, the compression surface of the second distal hole is oriented relative to an axis of the distal portion of the body so that, when the plate is placed in a desired position on a tibia, as a head portion of the second distal bone fixation element is slid along the sloped compression surface during insertion of the second distal bone fixation element into the second distal hole, the distal end of the body is moved caudally moving the proximal portion of the body to apply cranial compression.

The present disclosure also relates to a method for a Tibial Plateau Leveling Osteotomy (TPLO) which includes positioning a bone plate in a desired initial position with a first surface of the bone plate facing away from the tibia and a second surface thereof facing a tibia so that a proximal portion of the bone plate extends over a proximal tibial segment and a distal portion of the bone plate extends over a distal tibial segment that has been cut away from the proximal tibial segment and rotated and seated within a recess formed in the distal tibial segment when the proximal tibia segment was cut away; inserting a first distal bone fixation element into the distal tibial segment of the tibia via a first distal hole extending through the distal portion of the bone plate such that a head portion of the first distal bone fixation element is seated within a recess extending along a distal portion of the first distal hole; and inserting a second distal bone fixation element into the distal segment of the tibia via a second distal hole extending through the distal portion of the bone plate distally of the first distal hole so that a head portion of the second distal bone fixation element slides along a sloped compression surface extending along a side of the second distal hole to move the distal portion of the bone plate to rotate the bone plate about the first distal bone fixation element to apply compression of the proximal tibial segment against the distal tibial segment.

In an embodiment, the first and second distal holes are elongated in a direction parallel to a longitudinal axis of the distal portion of the bone plate.

In an embodiment, the method further includes inserting a first proximal bone fixation element through a first proximal hole and a second proximal bone fixation element through a second proximal hole into the proximal tibia segment, the first and second proximal holes extending through the proximal portion of the bone plate so that, when the plate is in the desired initial position, the first and second proximal bone fixation elements fix the proximal portion of the bone plate relative to the proximal tibial segment prior to insertion of the second distal bone fixation element through the second distal hole.

In an embodiment, the first proximal bone fixation element is inserted into a cranial side of the proximal tibial segment.

In an embodiment, inserting the first distal bone fixation element through the first distal hole includes inserting the first distal bone fixation element into a distal portion of the first distal hole so that the head portion of the first distal bone fixation element engages a relief of the first distal hole.

In an embodiment, the second distal bone fixation element is inserted through a groove formed in the sloped compression surface of the second distal hole proximate a distal end of the second distal hole so that the second distal bone fixation element is inserted into the second distal hole caudally of a central axis of the second distal hole.

In an embodiment, the method further includes inserting a third distal bone fixation element through a third distal hole extending through the distal portion of the bone plate, between the first and second distal holes, so that a head portion of the third distal bone fixation element slides along a sloped compression surface along a distal portion of the third distal hole to move a distal portion of the bone distally relative to the third distal bone fixation element to generate distal compression of the proximal tibial segment against the distal tibial segment.

In an embodiment, as the proximal tibial segment is being distally compressed against the distal tibial segment, the first and second distal bone fixation elements are moved toward proximal ends of the first and second distal holes, respectively.

In an embodiment, the compression surface of the second distal hole extends along a caudal side of the second distal hole so that insertion of the second distal bone fixation element into the second distal hole moves rotates the distal portion of the bone plate caudally to apply cranial compression of the proximal tibial segment against the distal tibial

BRIEF DESCRIPTION

FIG. 1 shows a perspective view of a TPLO bone plate according to an exemplary embodiment of the present disclosure;

FIG. 2 shows a longitudinal cross-sectional view of a first hole extending through a distal portion of the TPLO plate of FIG. 1;

FIG. 3 shows the longitudinal cross-section view of the first hole as shown in FIG. 2, with a first bone fixation element inserted therein;

FIG. 4 shows a plan view of a second hole extending through the distal portion of the TPLO plate of FIG. 1;

FIG. 5 shows the plan view of the second hole as shown in FIG. 4, with a second bone fixation element inserted therein along a caudal side thereof;

FIG. 6A shows a transverse cross-sectional view of the second hole as shown in FIG. 5;

FIG. 6B shows a transverse cross-sectional view of the second hole as shown in FIG. 5, with the second bone fixation element inserted therein;

FIG. 7 shows the plan view of the second hole as shown in FIG. 4, with the second bone fixation element moved toward a longitudinal axis of the distal portion;

FIG. 8 shows a transverse cross-sectional view of the second hole as shown in FIG. 7, with the second bone fixation element moved toward a longitudinal axis of the distal portion;

FIG. 12 shows a plan view of the TPLO plate according to the exemplary embodiment of FIG. 1, with the first bone fixation element inserted through the first hole;

FIG. 13 shows a plan view of the TPLO plate according to the exemplary embodiment of FIG. 1, with the second bone fixation element inserted through the second hole;

FIG. 14 shows a plan view of the TPLO plate according to the exemplary embodiment of FIG. 1, the plate rotated about the first bone fixation element; and FIG. 15 shows a plan view of the TPLO plate according to the exemplary embodiment of FIG. 1, with the third bone fixation element inserted through the third hole.

DETAILED DESCRIPTION

Figure 11:
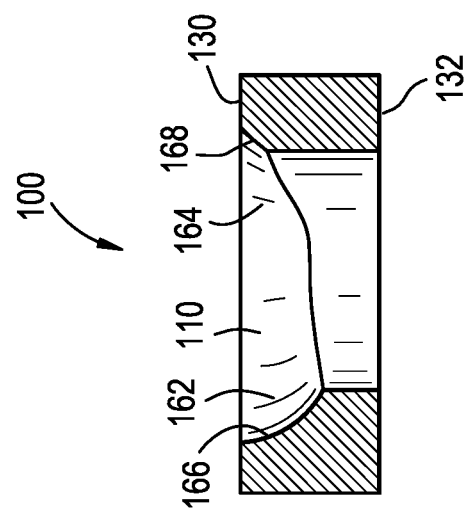
FIG. 11 shows a longitudinal cross-sectional view of a third hole extending through the distal portion of the TPLO plate of FIG. 1.

The present disclosure may be further understood with reference to the following description and the appended drawings, wherein like elements are referred to with the same reference numerals. The present disclosure relates to a Tibial Plateau Leveling Osteotomy (TPLO) plate and, in particular, relates to a TPLO plate configured to provide both cranial (i.e., transverse) and distal (i.e., axial) compression during a TPLO procedure. Exemplary embodiments of the present disclosure describe a TPLO plate comprising a proximal portion configured to be positioned over a cut and repositioned upper portion (e.g., proximal portion) of a tibia, and a distal portion configured to be positioned along a lower portion (e.g., distal portion) of the tibia.

The distal portion of the plate includes a first hole and a second hole extending therethrough, the first and second holes configured to work in concert to provide a cranial compression. In particular, the second hole may be positioned distally of the first hole. The first and second holes are configured so that, when first and second bone fixation elements are inserted through the first and second holes, respectively, the plate may be rotated about the first bone fixation element so that a distal end of the distal portion is moved in a caudal direction relative to the second bone fixation element and the proximal portion of the plate is moved in a cranial direction. This rotation of the plate provides cranial compression across the osteotomy cut.

The distal portion of the plate further includes a third hole extending therethrough, between the first and second holes. The third hole is configured, for example, as a compression hole which, when engaged via a third bone fixation element inserted therethrough, permits the plate to be moved distally relative to the tibia, resulting in a distal compression across the osteotomy cut. It will be understood by those of skill in the art that although the TPLO plates of the present embodiments are described with respect to a canine CCL, the TPLO plate of the present disclosure may also be used to treat the tibia of other quadrupeds such as, for example, felines, bovines, equines, etc. It will also be understood by those of skill in the art that the terms proximal, distal, caudal and cranial are anatomical directional terms for an animal such as, for example, a canine and are employed in a manner consistent with their standard anatomical meanings.

As shown in FIGS. 1-15, a TPLO plate 100 according to an exemplary embodiment of the present disclosure is configured to secure proximal and distal segments of a tibia which have been separated from one another during a TPLO procedure via a substantially curvilinear osteotomy cut as would be understood by those skilled in the art. During a TPLO procedure, a proximal segment of the tibia cut away from the rest of the tibia, rotated relative to the tibia to a new position selected to enhance the stability to, for example, a canine stifle joint (e.g., after injury to a cranial cruciate ligament (CCL)) and secured to the distal segment in this desired position.

According to an exemplary embodiment, the TPLO plate 100 comprises a body 101 including a proximal portion 102 sized and shaped to be positioned over the cut and repositioned proximal segment of the tibia, and a distal portion 104 sized and shaped to extend along the distal segment of the tibia so that the plate 100 fixes the position of the cut and repositioned portion of the tibia relative to the distal segment. In an exemplary embodiment, the distal portion 104 includes at least three holes (i.e., a first hole 106, a second hole 108, and a third hole 110) extending therethrough. The first hole 106 and the second hole 108 are configured to work together so that, when first and second bone fixation elements 112, 114 have been inserted therein, respectively, cranial (i.e., transverse) compression of the osteotomy cut is permitted as will be described in more detail below.

The third hole 110 extending through the distal portion 104 is, in this embodiment, configured as a distal compression hole so that, when a third bone fixation element 116 is inserted therein, axial (distal) compression of the osteotomy cut is permitted as will also be described in more detail below. The cranial and distal compression together ensure that the cut and repositioned proximal segment of the tibia is optimally seated within a recessed portion of the distal segment formed via the curvilinear cut to enhance a healing of the bone.

As shown in FIG. 1, the body 101 of the plate 100 extends longitudinally from a proximal end 126 to a distal end 128. The body 101 is defined via a first surface 130 which, in an operative configuration, faces away from a bone (e.g., the tibia), and a second surface 132 which, in the operative configuration faces toward the bone. The plate 100 includes the proximal portion 102 and the distal portion 104, which may be connected to one another via a neck portion 124 so that, when in the operative configuration, the proximal portion 102 is positioned over the proximal segment of the tibia as desired, the distal portion 104 extends over and along the distal segment of the tibia while the neck portion 124 extends across the interface between the cut-away portion of the proximal tibia and the distal tibia at the curvilinear osteotomy cut.

The distal portion 104 extends distally of the proximal portion 102 along a longitudinal axis L. In one embodiment, this neck portion 124 may be curved so that the proximal portion 102 is offset (e.g., angled) relative to the longitudinal axis L of the distal portion 104. For example, the proximal portion 102 may be angled in a caudal direction relative to the longitudinal axis L although, as would be understood by those skilled in the art, this angle may be selected in any manner desired to conform to the geometry of the cut-away and rotated portion of the tibia relative to the distal tibia (or any other bone segments involved) in any given procedure.

As will be understood by those of skill in the art, the proximal portion 102 is, in this embodiment, preferably constructed, sized, shaped and contoured to conform to the shape and orientation of the cut-away proximal segment of the tibia when the cut-away segment is in a desired position relative to the distal tibia and the distal portion 104 is in a desired position on the distal tibia. In particular, the second surface 132 of this embodiment is specifically contoured so that, when the proximal portion 102 is positioned over the proximal segment of the tibia, the second surface 132 extends along an exterior surface of the cut and rotated proximal segment of the tibia, in contact therewith.

In one embodiment (see FIG. 9), the proximal portion 102 includes at least three holes (i.e., a first hole 118, a second hole 120, and a third hole 122), each of which extends through the proximal portion 102 from the first surface 130 to the second surface 132, along an edge 134 extending along the proximal end 126 of the plate 100. Each of the first, second and third holes 118, 120, 122 of the proximal portion 102 of this embodiment is configured to receive therein a bone fixation element such as, for example, a locking screw to fix the proximal portion 102 of the plate 100 relative to the cut and rotated proximal segment of the tibia.

The first hole 118 is positioned on the plate 100 and oriented so that, when the plate 100 is positioned on a tibia in a desired position, the first hole 118 is positioned to receive a bone fixation element through a caudal portion of the proximal segment of the tibia while the second hole 120 is positioned and oriented to receive a bone fixation element through a proximal portion of the proximal segment of the tibia. The third hole 122 is positioned and oriented on the plate 100, when the plate 100 is in the desired position, to receive a bone fixation element through a cranial portion of the proximal segment of the tibia. As would be understood by those skilled in the art, central axes of each of the first, second and third holes 118, 120, 122 may be optionally angled to direct bone fixation elements inserted therealong into a desired portion of the proximal segment of the bone (e.g., a central mass of the cut-away portion of the proximal tibia).

Furthermore, any or all of the first, second and third holes 118, 120, 122 of the proximal portion 102 may be configured as locking holes, including a threading extending therein configured to engage corresponding threading on the head of a bone fixation element inserted therein. Thus, bone fixation elements inserted therein may be locking screws including corresponding threading along a head portion thereof. It will be understood by those of skill in the art, however, that the first, second and third holes 118, 120, 122 of the proximal portion 102 of the plate 100 may have any of a variety of configurations so long as bone fixation elements are insertable therethrough to be inserted into a desired portion of the bone.

The distal portion 104 of this embodiment is contoured to extend, when the plate 100 is in the desired position, along the distal segment of the tibia. In particular, in the operative configuration, the second surface 132 extends along the distal segment, in contact therewith. As described above, the distal portion 104 of this embodiment also at least includes three holes extending therethrough—the first hole 106, the second hole 108 and the third hole 110. The first hole 106 and the second hole 108 are configured to work together to permit the application of cranial compression across the osteotomy cut when engaged with the first and second bone fixation elements 112, 114. The third hole 110 is configured to permit the application of distal compression across the osteotomy cut when a third bone fixation element 116 is inserted into and engaged therewith.

The first hole 106 is positioned adjacent to a proximal end 136 of the distal portion 104, proximate the neck portion 124. The first hole 106 is shaped so that, when the first bone fixation element 112 is received therein, the plate 100 may be pivoted about the first bone fixation element 112. The spherical recess 142 is sized, shaped and configured to engage a head portion 113 of the bone fixation element 112. In particular, the first hole 106 according to this embodiment is configured so that when the first bone fixation element 112 is inserted along a central axis of the spherical recess 142 (the central axis being substantially normal to the portion of the first surface 130 extending around the recess 142), a head portion 113 of the first bone fixation element 112 contacts a surface of the recess 142 permitting the body 101 of the plate 100 to rotate about the first bone fixation element 112 around the central axis of the spherical recess 142. The first bone fixation element 112 in this embodiment may, for example, be a standard cortex screw.

As shown in FIGS. 2-3, the first hole 106 extends through the distal portion 104, from the first surface 130 to the second surface 132, along a central axis which extends, for example, substantially perpendicularly to one of the first and second surfaces 130, 132. In one embodiment, the central axis of the first hole 106 extends through the longitudinal axis L and is elongated along the longitudinal axis L. The first hole 106 includes a proximal portion 138 and a distal portion 140, each of which is configured to receive the first bone fixation element 112 therein as the plate 100 is moved relative to the first bone fixation element 112 as a result of distal compression. The proximal portion 138 includes a spherical recess 146 extending into the first surface 130 toward the second surface 132 along a central axis. A surface 144 of the spherical recess 146 is sized, shaped and configured to engage a head portion 113 of the bone fixation element 112.

In particular, the bone fixation element 112 is initially inserted into the distal portion 140 of the first hole 106 so that an underside of the head portion 113 of the bone fixation element 112 (i.e., a surface of the head portion 113 facing toward the bone) is seated within the spherical recess 142. When the head portion 113 of the first bone fixation element 112 is seated in the spherical recess 142, movement of the plate 100 relative to the tibia is constrained in multiple directions while permitting rotation of the plate 100 about the first bone fixation element 112 (and the central axis of the distal portion 140 of the first hole 106 within which the first bone fixation element 112 is received).

In one embodiment, the head portion 113 and the spherical recess 142 are configured so that, when the head portion 113 is received therein, inadvertent translational movement of the plate 100 relative to the tibia is prevented and, when the plate 100 is rotated about the first bone fixation element 112, the head 113 remains seated within the spherical recess 142. For example, the first hole 106 may be dimensioned relative to the diameter of a shaft of the first bone fixation element 112 so that the plate 100 is secured against all movement except rotation about the first bone fixation element 112. Translation along the axis L is prevented by the seating of the first bone fixation element 112 in the distal portion 140 until the first bone fixation element is slightly loosened as will be described in more detail below. This aids the physician in establishing and maintaining a desired initial axial position of the plate 100 until distal compression is applied as will be described below.

In this embodiment, the spherical recess 146 of the proximal portion 138 meets the spherical recess 142 of the distal portion 140 at a transition point 147 beyond which the head portion 113 of the first bone fixation element 112 will pass proximally only as distal compression is applied. As indicated above, this transition point 147 has a reduced width that holds the plate 100 in a desired axial position relative to the first bone fixation element 112 until the first bone fixation element 112 has been loosened and distal compression is applied via the third hole 110. The spherical recess 146 of the proximal portion 138 is thus open to the spherical recess 142 of the distal portion 140 of the first hole 106 at the transition point 147 which may be configured, for example, as a slot having a width (extent transverse to the axis L) that is reduced compared to the widths of the proximal portion 138 and the distal portion 140.

A surface 148 of the spherical recess 146 of the proximal portion 138 of the first hole 106 is also sized, shaped and configured to engage the head portion 113 of the first bone fixation element 112 in a seating configuration. The surface 144 of the spherical recess 142 of the distal portion 140 and the surface 148 of the spherical recess 146 of the proximal portion 138 form a substantially continuous surface. The first hole 106 therefore has a substantially slotted configuration so that the first bone fixation element 112 is translatable along the longitudinal axis L of the distal portion of the plate 100. Thus, during axial compression of the tibia, the plate 100 moves relative to the bone and the first bone fixation element 112 so that the first bone fixation element 112 is moved from the distal portion 140 of the first hole 106 toward the proximal portion 38.

More specifically, in an exemplary embodiment, the spherical recess 142 of the distal portion 140 and the spherical recess 146 of the proximal portion 138 are separated from one another by a clear transition point 147 (in this case a point of minimum width of the hole 106) that creates a generally binary positioning of the head of the first bone fixation element 112 inserted therein. That is, as the axial position of the plate 100 is adjusted (during axial compression), the head of the first bone fixation element 112 assists in establishing an initial axial position and then in locking a final axial position of the plate 100 (after a desired axial adjustment of the plate 100 has been completed) into a desired final axial position as the head 113 of the first bone fixation element 112 is held on the distal side of the transition point 147 (during initial positioning) and then on the proximal side of the transition point 147 after distal compression by the narrowing of the hole 106 at the transition point 147. This prevents the plate 100 from moving proximally so that head 113 of the first bone fixation element passes the transition point 147 after the increased forces applied during axial compression have been discontinued.

In general, after the first bone fixation element 112 has been loosened slightly and distal compression is being applied as described below, the first bone fixation element 112 will be pushed through and past the transition point 147 from the recess 142 into the recess 146. The narrowness of the hole 106 at the transition point 147 then interferes with the larger diameter of the head 113 of the first bone fixation element 112 to prevent the plate 100 from moving distally away from the desired final position (i.e., holding the plate 100 in a desired position relative to the first bone fixation element 112) to maintain the desired distal compression across the osteotomy.

According to an exemplary embodiment, the spherical recess 142 of the distal portion 140 and the spherical recess 146 of the proximal portion 138 have differing depths so that subsequent to the transverse compression and prior to the axial compression, the first bone fixation element 112 may be loosened to permit translational movement thereof within the first hole 106. In one embodiment, the spherical recess 146 extends deeper into the plate 100 (farther from the first surface 130 toward the second surface 132) than does the spherical recess 142 of the distal portion 140. In another embodiment, the spherical recess 146 extends into the plate 100 to a depth shallower than the spherical recess 142 of the distal portion 140. In one example, the distal and proximal portions 140, 138 of the first hole 106 differ in depth by approximately 0.2 mm. Alternatively, the spherical recess 142 of the distal portion 140 and the spherical recess 146 of the proximal portion 138 may have the same depth so long as they intersect to create a transition point 147 that operates to prevent inadvertent movement of the plate 100 relative to the first bone fixation element 112 as described above.

The second hole 108, as shown in FIGS. 4-8, is configured to receive the second bone fixation element 114 therein such that, as the second bone fixation element 114 is moved into increasing engagement with a portion of the second hole 108, the distal end 128 of the plate 100 is moved in a caudal direction relative to the second bone fixation element 114 rotating the plate 100 about the first bone fixation element 112, relative to the spherical recess 142. In particular, the head portion 113 of the first bone fixation element 112 remains seated within the spherical recess 142 of the distal portion 140 of the first hole 106. This rotation of the plate 100 moves the proximal portion 102 in a cranial direction, thereby providing cranial compression of the cut-away and repositioned proximal segment of the tibia against the distal segment of the tibia. The second hole 108 of the distal portion 104 of the plate 100 is, in this embodiment positioned distally of the first hole 106, proximate the distal end 128 of the plate 100 although the second hole 108 could be positioned proximally of the first hole 106 if the orientation of the various elements of such an alternate second hole 108 were made a mirror image (relative to the axis L) of the second hole 108 of this embodiment.

The second hole 108 extends through the distal portion 104, from the first surface 130 to the second surface 132, and is, in this embodiment, substantially aligned with the first hole 106 along the longitudinal axis L of the distal portion 104. Similarly to the first hole 106, the second hole 108 is elongated along the longitudinal axis L from a proximal end 160 to a distal end 158. The second hole 108 includes a relief 150 into the plate from the first surface 130 toward the second surface 132. A surface 152 of the relief 150 includes a head receiving portion 155 and a compression portion 154. The head receiving portion 155 is configured to engage an underside of a head portion 115 of the second bone fixation element 114 after compression.

In one embodiment, the head receiving portion 155 is curved (e.g., forming a part of a sphere or a cylinder) while the compression portion 154 is sloped and substantially planar to permit the head portion 115 of the second bone fixation element to slide over the compression portion 154 as the second bone fixation element 114 is inserted into the bone. The angling of the sloped surface of the compression portion 154 relative to the axis of the second bone fixation element 114 (inserted, for example along a central axis of the second hole 108) translates motion of the head portion along the central axis of the second hole 108 into motion of the compression portion 154 and the distal portion of the plate 100 lateral to the longitudinal axis L of the distal portion of the plate 100.

In one embodiment, the plane of the compression portion 154 is substantially parallel to the longitudinal axis of the plate 100 and angled relative to the central axis of the second hole 108 so that, as the second bone fixation element 114 is inserted further into the bone, the head portion 115 drives the distal portion of the plate 100 further caudally. In one embodiment, the central axis of the second hole 108 is orthogonal to the axis L so that the plane including the sloped compression surface 154 intersects the plane including the central axis of the second hole 108 and the axis L at an angle selected to achieve a desired ratio of compression distance to distance of insertion of the second bone fixation element 114 into the second hole 108.

In one embodiment, the compression portion 154 of the surface 152 extends along a caudal side of the second hole 108. The compression portion 154 is sloped (e.g., compression portion 154 is substantially planar to facilitate sliding of the head portion 115 therealong) and extends along an incline at an angle selected so that, as the second bone fixation element 114 is moved further into the second hole 108, the underside of the head portion 115 is pressed against and slides along the compression portion 154 moving the distal portion of the plate 100 in a caudal direction relative to the second bone fixation element 114 (i.e., the distal portion of the plate 100 moves caudally relative to the second bone fixation element 114 so that, as the plate rotates about the first bone fixation element 112, the proximal portion of the plate 100 moves cranially to apply cranial compression across the osteotomy).

The planar nature of the surface 154 generates a linear relation between the amount of rotation of the screw (corresponding to a depth of insertion of the screw) to the amount of translation of the plate 100, facilitating the generation of a desired amount of compression. Thus, the angle of the surface 154 can be altered in relation to the geometry of the underside of the head portion 115 of the second bone fixation element 114 to generate a desired ratio between depth of insertion of the second bone fixation element 114 and the amount of compression applied. Those skilled in the art will understand that, although the plate 100 is actually rotating about the first bone fixation element 112 and the distal portion of the plate 100 is moving along a portion of a circle, the small size of the caudal compression distance compared to the radius about which the plate 100 is rotating (distance between the first and second bone fixation elements 112, 114, respectively) renders the compression (movement of the proximal portion of the plate 100) substantially linear in the cranial direction.

In an embodiment, the surface 152 of the relief 150 also includes a groove 156 extending into the sloped compression portion 154 proximate a distal end 158 of the second hole 108. This groove 156 is configured to permit insertion of the second bone fixation element 114 into the distal end 158 of the second hole 108 in a position offset from the longitudinal axis L of the distal portion 104, toward a caudal side of the second hole 108, as shown in FIGS. 5-6. Thus, as the second bone fixation element 114 is inserted thereinto, the head portion 115 of the second bone fixation element 114 engages and slides along the compression portion 154 (e.g., at a point P generally aligned with a center of the groove 156), moving the distal end 128 of the bone plate in a caudal direction relative to the second bone fixation element 114, as shown in FIGS. 7-8, with the second bone fixation element 114 moving toward the longitudinal axis L to be seated within the head receiving portion 155 as the plate 100 is rotated about the first bone fixation element 112 received within the first hole 106.

This rotation of the plate 100 moves the proximal portion 102 in a cranial direction relative to the tibia, applying a cranial compression of the proximal segment of the tibia across the osteotomy against the distal segment of the tibia. Furthermore, a width W of the sloped compression portion (e.g., an extent of the compression portion 154 in a proximal-distal direction) is preferably selected to be at least as great as a maximum amount of axial compression to be applied to the plate 100. That is, the compression portion 154 is preferably made wide enough so that, as the plate is translated proximally along the longitudinal axis of the plate during axial compression, the point of contact between the underside of the head portion 115 of the second bone fixation element 114 and the surface 152 remains within this width W. As would be understood by those skilled in the art, the width W of the compression portion 154 may be made longer than this difference to accommodate any error in the placement of the second bone fixation element 114.

Figure 10:
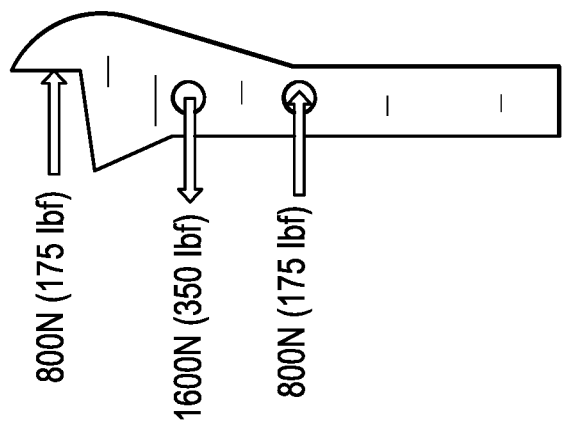
FIG. 10 shows a schematic drawing showing force vectors on a tibia according to the exemplary plate of FIG. 1.
Figure 9:
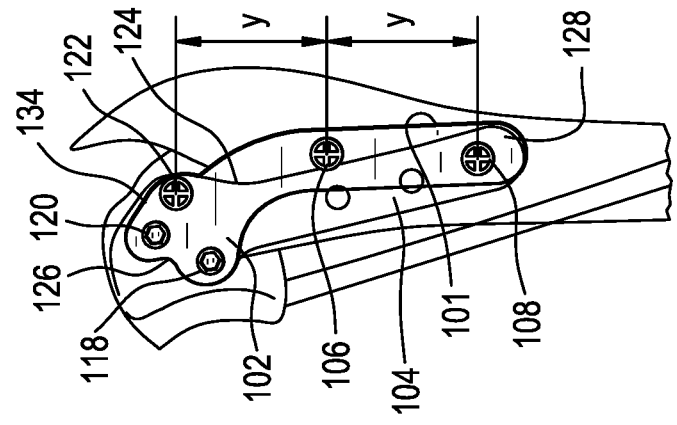
FIG. 9 shows a schematic drawing of the plate according to the exemplary embodiment of FIG. 1, positioned over a tibia.

In one embodiment, as shown in FIG. 9, the second hole 108 of the distal portion 104 is separated from the first hole 106 of the distal portion 104 via a distance equal to a distance between the first hole 106 and the third hole 122 of the proximal portion 102. Thus, when the distal end 128 of the plate 100 is moved in a caudal direction and the plate 100 rotates about the first bone fixation element 112 inserted into the first hole 106, the proximal portion 102 of the plate 100 is moved in a cranial direction via a corresponding distance to provide compression across the osteotomy. Accordingly, as shown in FIG. 10, a cranial compression force exerted on the tibia is equal to a force exerted on the plate 100 via the second bone fixation element 114 inserted through the second hole 108 of the distal portion 104.

The third hole 110, as shown in FIG. 11, extends through the distal portion 104 in a position extending between the first and second holes 106, 108 and is configured to receive a third bone fixation element 116. In one embodiment, the third hole 110 is positioned midway between the first and second holes 106, 108. The third hole 110 in this embodiment is substantially aligned with the first and second holes 106, 108 along the longitudinal axis L and may be similarly elongated along the longitudinal axis L. In one embodiment, the third hole 110 is a dynamic compression hole configured to provide distal compression across the osteotomy. For example, the third hole 110 extends through the distal portion 104 from the first surface 130 to the second surface 132 and, similarly to the first hole 106, includes a proximal portion 162 and a distal portion 164, which facilitates translational movement of the third bone fixation element 116 therewithin from the distal portion 164 toward the proximal portion 162, as axial compression is being applied to the tibia.

In one embodiment, the proximal portion 162 includes a spherical relief 166 extending into a thickness of the plate from the first surface 130. The spherical relief 166 is sized and shaped to correspond to an underside of a head portion of the third bone fixation element 116 which, in an exemplary embodiment, may be a standard cortex screw. Thus, the spherical relief 166 may be configured to seat the head portion of the third bone fixation element 116 therein. When the head portion of the third bone fixation element 116 is seated in the spherical relief 166, the head portion of the bone fixation element 116 may be substantially flush with the first surface 130 of the plate 100 as would be understood by those skilled in the art. It will be understood by those of skill in the art, however, that the head portion of the third bone fixation element 116 is not required to be finally seated within the spherical relief 166. The third bone fixation element 116 may be moved from the distal portion 164 toward the proximal portion 162 by a distance corresponding to a desired axial compression.

The distal portion 164 includes a sloped compression surface 168 inclined at a curve/angle selected so that, as the head portion of the third bone fixation element 116 is pressed thereagainst (e.g., as the third bone fixation element 116 is inserted gradually further into the bone and further through the plate 100), the sloped compression surface 168 slides along the head portion of the third bone fixation element 116. In particular, as the third bone fixation element 116 is driven more deeply into the bone, the head portion of the third bone fixation element 116 slides along the sloped compression surface 168 moving the plate 100 in a distal direction relative to the third bone fixation element 116 applying distal compression across the osteotomy—i.e., the proximal segment of the tibia is pressed distally against the distal segment of the tibia as the proximal portion of the plate 100 (coupled to the cut-away proximal segment of the tibia) is drawn distally by the movement of the distal portion of the plate 100.

According to an exemplary method, the plate 100 may be used to provide both cranial and distal compression during a TPLO procedure. As will be understood by those of skill in the art, upon cutting of a proximal segment of a tibia from a distal segment of the tibia via a substantially curvilinear osteotomy, the proximal segment is rotated and repositioned relative to the distal segment and the plate 100 is then be placed over the separated bone segments so that the proximal portion 102 is positioned over the cut and repositioned proximal segment of the tibia and the distal portion 104 is positioned over the distal segment of the tibia.

According to the exemplary method, as shown in FIG. 12, the first bone fixation element 112 is first inserted into the distal portion 140 of the first hole 106 so that the head portion 113 of the first bone fixation element 112 is seated within the spherical recess 142 thereof. As shown in FIG. 13, the second bone fixation element 114 is then inserted through the groove 156 of the second hole 108 so that the head portion 115 of the second bone fixation element 114 contacts the compression portion 154 of the second hole 108. Insertion of the first and second bone fixation elements 112, 114, as described above, establishes a preliminary position of the bone plate 100 which is then adjusted as described below. It will be understood by those of skill in the art that bone fixation elements are then inserted through at least two of the holes extending through the proximal portion 102 of the plate 100 to fix the proximal portion 102 relative to the proximal segment of the tibia. In one embodiment, bone fixation elements are inserted through a cranial one of the holes (e.g., third hole 122) and one of the other holes (e.g., the first hole 118 and the second hole 120) of the proximal portion 102.

As discussed above, as the second bone fixation element 114 is tightened (e.g., rotatably inserted further into the second hole 108), the compression portion 154 slides along the head portion 115 so that the distal end 128 of the plate 100 is moved in a caudal direction relative to the second bone fixation element 114, as shown in FIG. 14. As the distal end 128 is moved in a caudal direction relative to the second bone fixation element 114, the plate 100 rotates about the first bone fixation element 112 that was previously inserted into the first hole 106, so that the proximal portion 102 of the plate is correspondingly being moved in a cranial direction. Thus, the proximal segment of the tibia, to which the proximal portion 102 is fixed, is being cranially compressed against the distal segment of the tibia across the osteotomy.

After cranial compression of the tibia has been fully applied, the third bone fixation element 116 is inserted into the distal portion 164 of the third hole 110, as shown in FIG. 15. As the third bone fixation element is inserted further through the third hole 110, the head portion of the third bone fixation element 116 slidingly engages the compression surface 168 thereof, moving the plate 100 in a distal direction relative to the third bone fixation element 116. Thus, the proximal segment of the tibia, to which the proximal portion 102 is fixed, is distally compressed against the distal segment of the tibia.

As the osteotomy is being distally compressed, the third bone fixation element 116 is moved relative to the third hole 110 toward the proximal portion 162 of the third hole 110. It will be understood by those of skill in the art that, during distal compression, the first bone fixation element 112 is similarly being received within the proximal portion 138 of the first hole 106 while the second bone fixation element 114 is moving toward the proximal end 160 of the second hole 108. Upon completion of the distal compression, the first and second bone fixation elements 112, 114 may be tightened and additional bone fixation elements may be inserted through any remaining holes extending through, for example, the proximal portion 102, to provide further locking of the plate 100 in the desired position relative to the tibia.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A Tibial Plateau Leveling Osteotomy (TPLO) plate, comprising:
a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion configured to be positioned over a distal segment of the tibia during the TPLO procedure;
a first distal hole extending through a proximal end of the distal portion of the body from the first surface to the second surface, the first distal hole configured to receive a first distal bone fixation element therein so that the body is rotatable about the first distal bone fixation element relative to a recess of the first distal hole within which a head portion of the first distal bone fixation element is configured to be seated; and
a second distal hole extending through the distal portion of the body distally of the first distal hole from the first surface to the second surface, the second distal hole including a sloped compression surface, the second distal hole being configured to receive a second distal bone fixation element therein so that when a head portion of the second distal bone fixation element is slid along the sloped compression surface during insertion of the second distal bone fixation element into the second distal hole, the distal end of the body is moved so that an intersection of the sloped compression surface and the first surface of the body move away from an axis of the second distal bone fixation element rotating the body about the first distal bone fixation element to provide a desired movement of the proximal portion of the body to achieve a desired compression between the cut and repositioned proximal segment of a tibia and the distal segment of the tibia, wherein the second distal hole further includes a groove extending into the sloped compression surface proximal of a distal end of the second distal hole, the groove configured to permit insertion of the second distal bone fixation element through the second distal hole along a caudal side of the longitudinal axis of the distal portion of the body.

2. The plate of claim 1, wherein the first distal hole is elongated along a longitudinal axis of the distal portion of the body, the first distal hole including a distal portion including a first rounded relief configured to seat the head portion of the first distal bone fixation element so that, when the first distal bone fixation element is received within the distal portion of the first distal hole, the body is rotatable thereabout.

3. The plate of claim 2, wherein the first distal hole includes a proximal portion including a second rounded relief configurated to seat the head portion of the first distal bone fixation element after a desired axial compression has been applied.

4. The plate of claim 3, wherein the first and second rounded reliefs of the first distal hole are separated from one another by a transition point that provides resistance to passage of the head of a bone fixation therethrough.

5. The plate of claim 4, wherein the transition point is a point at which a width of the first distal hole in a direction transverse to a longitudinal axis of the distal portion of the body is a minimum.

6. The plate of claim 1, wherein each of the first and second distal holes is elongated in a direction parallel to a longitudinal axis of the distal portion of the body.

7. The plate of claim 1, further comprising a third distal hole extending through the distal portion of the body, between the first and second distal holes, the third distal hole being configured to receive a third distal bone fixation element therein.

8. The plate of claim 7, wherein the third distal hole is elongated in a direction parallel to a longitudinal axis of the distal portion of the body.

9. The plate of claim 7, wherein the third distal hole is configured as a dynamic compression hole including a sloped compression surface along a distal portion thereof so that, when the third distal bone fixation element is inserted through a distal portion of the third distal hole, a head portion of the third distal bone fixation element interfaces with the sloped compression surface of the third distal hole to move the body distally relative to the third distal bone fixation element to provide distal compression of the proximal segment of the tibia against the distal segment of the tibia.

10. The plate of claim 1, wherein the proximal portion of the body includes three proximal holes, each of which extends through the proximal portion, from the first surface to the second surface, along a proximal edge thereof, each of the proximal holes being configured to receive a proximal bone fixation element therein.

11. The plate of claim 10, wherein a first one of the three proximal holes extends through the proximal portion in a position configured to facilitate insertion of a first one of the proximal bone fixation elements therethrough into a caudal portion of the proximal segment of the tibia, wherein a second one of the proximal holes extends through the proximal portion in a position configured to facilitate insertion of a second one of the proximal bone fixation elements therethrough into a proximal portion of the proximal segment of the tibia, and wherein a third one of the proximal holes extends through the proximal portion in a position configured to facilitate insertion of a third one of the proximal bone fixation elements therethrough into a cranial portion of the proximal segment of the tibia.

12. The plate of claim 1, wherein the proximal portion of the body is connected to the distal portion of the body via a neck portion curved such that the proximal portion of the body is offset relative to the distal portion of the body toward a caudal side of a longitudinal axis of the distal portion of the body.

13. The plate of claim 1, wherein the compression surface of the second distal hole is oriented relative to an axis of the distal portion of the body so that, when the plate is placed in a desired position on a tibia, as a head portion of the second distal bone fixation element is slid along the sloped compression surface during insertion of the second distal bone fixation element into the second distal hole, the distal end of the body is moved caudally moving the proximal portion of the body to apply cranial compression.

14. A Tibial Plateau Leveling Osteotomy (TPLO) plate, comprising:

a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion configured to be positioned over a distal segment of the tibia during the TPLO procedure;

a first distal hole extending through a proximal end of the distal portion of the body from the first surface to the second surface, the first distal hole configured to receive a first distal bone fixation element therein so that the body is rotatable about the first distal bone fixation element relative to a recess of the first distal hole within which a head portion of the first distal bone fixation element is configured to be seated; and a second distal hole extending through the distal portion of the body distally of the first distal hole from the first surface to the second surface, the second distal hole including a sloped compression surface, the second distal hole being configured to receive a second distal bone fixation element therein so that when a head portion of the second distal bone fixation element is slid along the sloped compression surface during insertion of the second distal bone fixation element into the second distal hole, the distal end of the body is moved so that an intersection of the sloped compression surface and the first surface of the body move away from an axis of the second distal bone fixation element rotating the body about the first distal bone fixation element to provide a desired movement of the proximal portion of the body to achieve a desired compression between the cut and repositioned proximal segment of a tibia and the distal segment of the tibia, wherein the proximal portion of the body includes three proximal holes, each of which extends through the proximal portion, from the first surface to the second surface, along a proximal edge thereof, each of the proximal holes being configured to receive a proximal bone fixation element therein; and wherein a distance between the second distal hole and the first distal hole is equal to a distance between the first distal hole and the third proximal hole.

15. A method for a Tibial Plateau Leveling Osteotomy (TPLO), comprising:

positioning a bone plate in a desired initial position with a first surface of the bone plate facing away from the tibia and a second surface thereof facing a tibia so that a proximal portion of the bone plate extends over a proximal tibial segment and a distal portion of the bone plate extends over a distal tibial segment that has been cut away from the proximal tibial segment and rotated and seated within a recess formed in the distal tibial segment when the proximal tibia segment was cut away;

inserting a first distal bone fixation element into the distal tibial segment of the tibia via a first distal hole extending through the distal portion of the bone plate such that a head portion of the first distal bone fixation element is seated within a recess extending along a distal portion of the first distal hole; and inserting a second distal bone fixation element into the distal segment of the tibia via a second distal hole extending through the distal portion of the bone plate distally of the first distal hole so that a head portion of the second distal bone fixation element slides along a sloped compression surface extending along a side of the second distal hole to move the distal portion of the bone plate to rotate the bone plate about the first distal bone fixation element to apply compression of the proximal tibial segment against the distal tibial segment, wherein the second distal hole further includes a groove extending into the sloped compression surface proximal of a distal end of the second distal hole, and wherein inserting the second distal bone fixation element into the distal segment of the tibia further comprises inserting the second distal bone fixation element through the second distal hole along a caudal side of the longitudinal axis of the distal portion of the body via the groove.

16. The method of claim 15, wherein the first and second distal holes are elongated in a direction parallel to a longitudinal axis of the distal portion of the bone plate.

17. The method of claim 15, further comprising inserting a first proximal bone fixation element through a first proximal hole and a second proximal bone fixation element through a second proximal hole into the proximal tibia segment, the first and second proximal holes extending through the proximal portion of the bone plate so that, when the plate is in the desired initial position, the first and second proximal bone fixation elements fix the proximal portion of the bone plate relative to the proximal tibial segment prior to insertion of the second distal bone fixation element through the second distal hole.

18. The method of claim 17, wherein the first proximal bone fixation element is inserted into a cranial side of the proximal tibial segment.

19. The method of claim 15, wherein inserting the first distal bone fixation element through the first distal hole includes inserting the first distal bone fixation element into a distal portion of the first distal hole so that the head portion of the first distal bone fixation element engages a relief of the first distal hole.

20. The method of claim 15, wherein the second distal bone fixation element is inserted through a groove formed in the sloped compression surface of the second distal hole proximate a distal end of the second distal hole so that the second distal bone fixation element is inserted into the second distal hole caudally of a central axis of the second distal hole.

21. The method of claim 15, further comprising inserting a third distal bone fixation element through a third distal hole extending through the distal portion of the bone plate, between the first and second distal holes, so that a head portion of the third distal bone fixation element slides along a sloped compression surface along a distal portion of the third distal hole to move a distal portion of the bone distally relative to the third distal bone fixation element to generate distal compression of the proximal tibial segment against the distal tibial segment.

22. The method of claim 21, wherein, as the proximal tibial segment is being distally compressed against the distal tibial segment, the first and second distal bone fixation elements are moved toward proximal ends of the first and second distal holes, respectively.

23. The method of claim 15, wherein the compression surface of the second distal hole extends along a caudal side of the second distal hole so that insertion of the second distal bone fixation element into the second distal hole moves rotates the distal portion of the bone plate caudally to apply cranial compression of the proximal tibial segment against the distal tibial segment.

* * * * *